(12) United States Patent
Asplund et al.

(10) Patent No.: US 8,092,073 B2
(45) Date of Patent: Jan. 10, 2012

(54) SEPARATION MEDIA SLURRY TANK

(75) Inventors: Magnus Asplund, Uppsala (SE); Rolf Hjorth, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 436 days.

(21) Appl. No.: 12/517,447

(22) PCT Filed: Dec. 18, 2007

(86) PCT No.: PCT/SE2007/001125
§ 371 (c)(1),
(2), (4) Date: Jun. 3, 2009

(87) PCT Pub. No.: WO2008/082339
PCT Pub. Date: Jul. 10, 2008

(65) Prior Publication Data
US 2010/0044323 A1    Feb. 25, 2010

(30) Foreign Application Priority Data
Jan. 2, 2007 (SE) ..................................... 0700014

(51) Int. Cl.
*B01F 5/00*    (2006.01)
*G01N 30/56*    (2006.01)

(52) U.S. Cl. ..................... 366/136; 366/137; 366/168.1; 366/172.2

(58) Field of Classification Search ................ 366/136, 366/137, 168.1, 172.2
See application file for complete search history.

(56) References Cited

U.S. PATENT DOCUMENTS
2,365,293 A * 12/1944 Robinson ..................... 210/125
(Continued)

FOREIGN PATENT DOCUMENTS
DE    101 37 613    2/2003
(Continued)

*Primary Examiner* — Yogendra Gupta
*Assistant Examiner* — Emmanuel S Luk

(57) ABSTRACT

A tank adapted to be used for suspending separation media slurry before transferring the separation media slurry to a column or a container comprises:
  an impeller (7) adapted to rotate in order to mix the media slurry,
  a nozzle (9) provided protruding into the tank from the bottom (8) thereof, and
  an adjustable pipe (5) having an open end (6) positioned in the tank and which can be adjusted in position. The nozzle (9) and the adjustable pipe (5) are adapted to be connected to a pump (3) adapted to pump liquid from the adjustable pipe (5) when the open end (6) of the adjustable pipe (5) has been positioned in an uppermost liquid phase provided in the tank when the media slurry has started to sediment and pump the liquid, possibly containing a small amount of media, through the nozzle (9) back into the tank from the tank bottom (8) in order to start re-suspending media that has sedimented in the tank.

7 Claims, 2 Drawing Sheets

U.S. PATENT DOCUMENTS

| | | | | |
|---|---|---|---|---|
| 2,516,884 A * | 8/1950 | Kyame | ............................ | 127/28 |
| 2,900,176 A * | 8/1959 | Krogel | ........................... | 366/137 |
| 3,202,281 A * | 8/1965 | Weston | ........................... | 209/166 |
| 3,266,871 A * | 8/1966 | Kenkichi et al. | ............... | 422/253 |
| RE27,681 E * | 6/1973 | Gaddis | ........................ | 366/153.1 |
| 3,773,302 A * | 11/1973 | Johnson et al. | ............. | 366/164.6 |
| 4,325,642 A * | 4/1982 | Kratky et al. | .................. | 366/137 |
| 4,466,082 A * | 8/1984 | Zoschak et al. | ................ | 366/101 |
| 4,621,928 A * | 11/1986 | Schreiber | ...................... | 366/137 |
| 4,732,434 A * | 3/1988 | Hartrum | ....................... | 312/221 |
| 4,882,098 A * | 11/1989 | Weetman | ......................... | 261/93 |
| 5,169,750 A * | 12/1992 | Vacca | ........................... | 430/569 |
| 5,334,496 A * | 8/1994 | Pond et al. | .................... | 430/569 |
| 5,403,088 A * | 4/1995 | Killmer et al. | ................. | 366/102 |
| 6,513,965 B2 * | 2/2003 | Hasberg et al. | ............. | 366/168.1 |
| 7,367,651 B2 * | 5/2008 | Kang | ............................... | 347/43 |
| 7,810,674 B2 * | 10/2010 | Belongia et al. | ................ | 222/64 |
| 2010/0080077 A1 * | 4/2010 | Coy | ............................... | 366/137 |

FOREIGN PATENT DOCUMENTS

| | | |
|---|---|---|
| EP | 0 515 955 | 12/1992 |
| JP | 4323557 | 11/1992 |
| WO | WO 93/13937 | 7/1993 |
| WO | W099/64130 | 12/1999 |
| WO | WO 02/10739 | 2/2002 |

* cited by examiner

SEPARATION MEDIA SLURRY TANK

CROSS-REFERENCE TO RELATED APPLICATIONS

This application is a filing under 35 U.S.C. §371 and claims priority to international patent application number PCT/SE2007/001125 filed Dec. 18, 2007, published on Jul. 10, 2008, as WO 2008/082339, which claims priority to patent application number 0700014-4 filed in Sweden on Jan. 2, 2007.

FIELD OF THE INVENTION

The present invention relates to a method and a tank for suspending separation media slurry before transferring the slurry to a column or container.

BACKGROUND OF THE INVENTION

Separation media could be for example chromatography media and density gradient media. The media could be for example resins based on natural or synthetic polymer particles or inorganic material. For chromatography the separation media needs to be provided into a chromatography column. For the transportation of the separation media into for example a column the media needs first to be suspended into an homogenous media slurry mixture. The separation media is normally suspended with a liquid, for example water, buffer or a solvent. This suspended media is usually called media slurry. When a column should be filled with media slurry from a storage container, an intermediate tank is used where the slurry is mixed into a homogenous mixture. The media slurry is often stirred manually in the tank and it is important that the media slurry becomes a homogenous mixture regarding the distribution of different sizes of particles in the media. Of course it is not convenient to stir manually especially when there is a large amount of media slurry to be stirred. It could also take quite a long time to fill the column with the media slurry and the media slurry needs to be stirred the whole time. Another way to mix the slurry that is sometimes used is to shake or tilt the tank back and forth. This could be advantageous for small tanks and small volumes of slurry but is hard to perform and not suitable for big, heavy tanks.

Solutions have been proposed, for example in EP0515955 or JP4323557, where permanent, electrical stirrers, also called impellers are used. There are however different problems associated with these kind of impellers. If the impeller is not running the whole time when the media slurry is inside the tank the slurry will sediment and then it will be hard to start the impeller in the sedimented media. This requires furthermore an oversized engine. When starting the impeller in sedimented media the media particles can be damaged because of shear forces provided by the impeller. It could be preferable to not run the impeller the whole time in order to minimize possible damage to the particles caused by the impeller.

SUMMARY OF THE INVENTION

An object of the present invention is to provide an improved method and tank for suspending separation media slurry before transportation of said media slurry into for example a column where particles in said media are not damaged.

Hereby the impeller does not need to start in a thick, sedimented media with the risk of damaging particles in the media and the impeller does not need to be running the whole time when the separation media is inside the tank. The spraying of liquid by the nozzle starts the re-suspension of the media from the bottom of the tank and the impeller can be started when the media has been sufficiently re-suspended. Furthermore liquid from the liquid phase of the media slurry having started to sediment is used for the spraying by the nozzle and hereby no new liquid need to be added and hereby the slurry concentration can be kept constant.

Further suitable embodiments are described in the dependent claims.

DETAILED DESCRIPTION OF THE INVENTION

Figure 1:
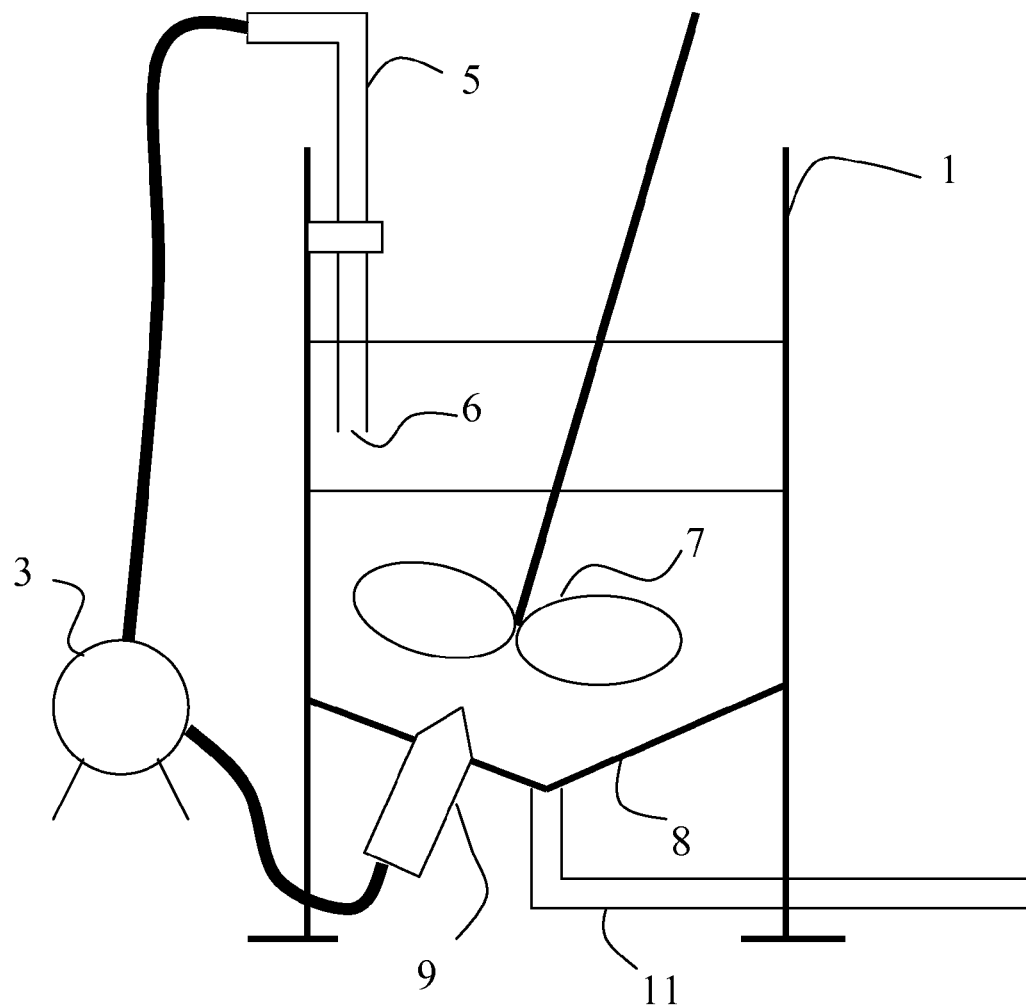
FIG. 1 is a schematic view of a separation media slurry tank according to the invention.
Figure 2:
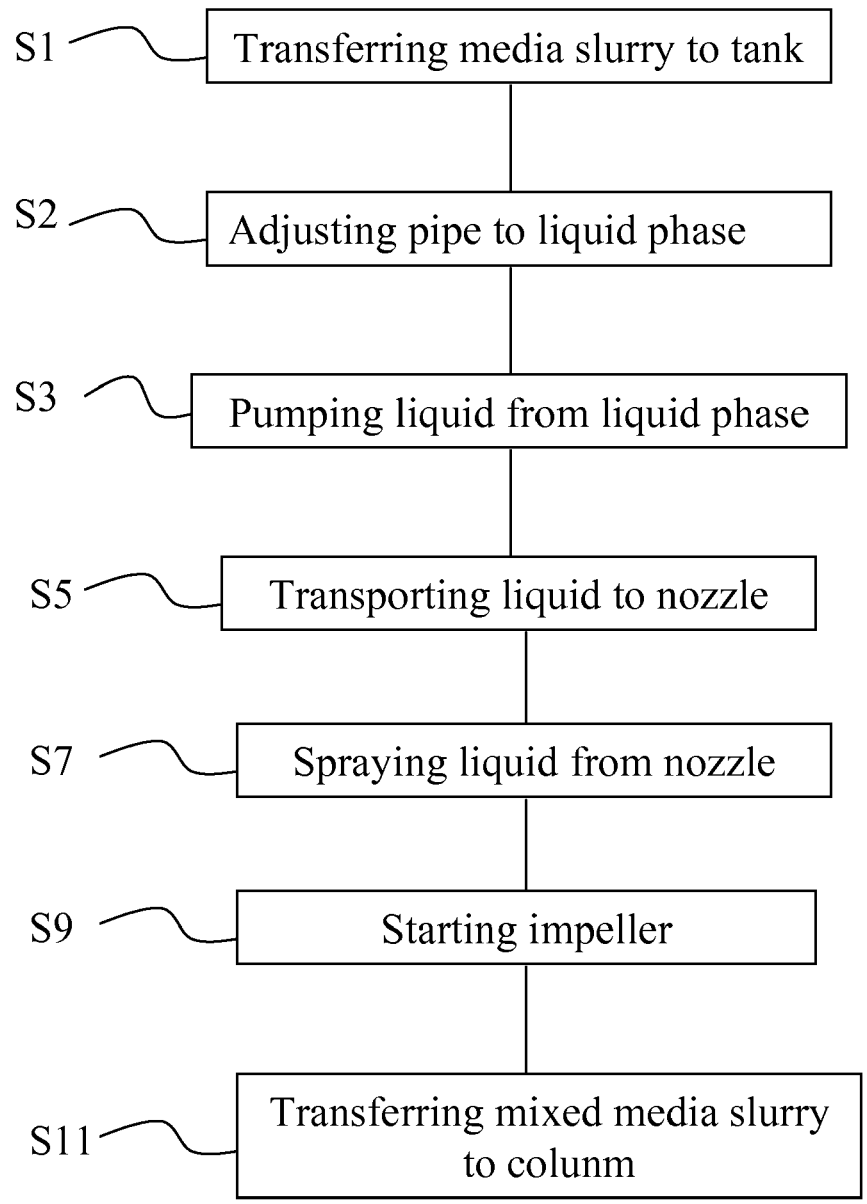
FIG. 2 is a flow chart describing the steps of the method.

FIG. 1 is a schematic view of a separation media slurry tank 1 according to the invention. If media is to be fed to a column from a media storage container the media is first transferred from the storage container to a media tank according to the invention. This could be done by connecting a tube from the storage container to a pump 3 provided in connection with the media slurry tank. Said pump is further connected to an adjustable pipe 5 that has an open end 6 provided inside the tank 1. Said adjustable pipe 5 is further described below. Hereby the media slurry can be pumped from the media storage container to the tank. Alternatively the media could be transferred from the storage container to the tank using another pump and some other tubes or pipes.

When the media has been transferred to the tank it immediately starts to sediment. An impeller 7 that is provided inside the tank can be started from the beginning and keep on stirring the media slurry the whole time until the media has been transferred to a column where it should be used for, for example chromatography, but according to the invention, as will be further described below, the impeller does not need to be ongoing the whole time. The impeller 7 is preferably designed as a coil in the height direction of the tank, this kind of impeller is also called a helical ribbon. Other designs such as a two -or three-bladed propeller or an impeller formed as an anchor are however also possible. In FIG. 1 a two-bladed propeller 7 is shown. Furthermore the impeller is suitably provided with its lowest end close to the bottom 8 of the tank.

According to the invention a nozzle 9 is furthermore provided protruding into the tank from the bottom 8 of the tank. This nozzle is connected to the pump 3, which in turn is connected to the adjustable pipe 5 as described above. The adjustable pipe 5 can be adjusted to have its open end 6 in a liquid phase provided above the sedimented media as soon as the media slurry is starting to sediment. According to the invention the pump 3 pumps liquid from the liquid phase, through the adjustable pipe 5 and further to the nozzle 9. The pump applies a pressure to the liquid in the nozzle and the nozzle is designed such that the liquid is introduced with some speed, such as spraying, into the sedimented media from the bottom 8 of the tank. This has the advantage that the sedimented media in the tank will start to re-suspend. Preferably the impeller is not started until the sedimented media has been sufficiently re-suspended by the spraying from the nozzle. Hereby it will be easier to start the impeller than it would have been if the impeller would have to start inside thick, sedimented media and the risk for damaging particles of the media is minimized. Furthermore the use of the liquid from the liquid phase of the sedimented media slurry for the spraying by the nozzle implies that no extra liquid need to be provided and the media slurry concentration can be kept constant.

When the media slurry has been stirred and mixed enough it can be transferred to a column through a pipe 11 from the bottom of the tank 1.

The tank according to the invention can also be used when transferring media from a column to a storage container. It could be suitable to first transfer the media to the tank, suspend the media sufficiently according to what was previously described and then transfer the media slurry to the storage container.

The method according to one embodiment of the invention where media slurry is transferred from a storage container to a column via the tank will now be further described with reference to the flowchart in FIG. 2. The steps are described in order below.

S1: Media slurry is first transferred from the storage container to the tank according to the invention. This could be done by using a pump and a tube or pipe. Possibly a pump 3 connected to the tank and the adjustable pipe 5 of the tank can be used for this transferring of media slurry from the storage container to the tank. As soon as the media slurry has entered the tank it starts to sediment—actually it is already sedimented to some degree since no stirring has been performed in the storage container, i.e. media will sediment at the bottom 8 of the tank and a liquid phase (possibly containing some particles also) will be built up over the sedimented media.

The method steps S2-S11 need not to be performed immediately after transferring of the media slurry to the tank. But when it is time for the transferring of the media slurry to the column the media slurry needs to be mixed into an homogenous media slurry and then the steps S2-S11 will be performed.

S2: The adjustable pipe 5 is adjusted such that its open end 6 is in the liquid phase in the tank.

S3: The next step is to pump liquid from the liquid phase through the adjustable pipe 5 by using the pump 3.

S5: The liquid is then transported through the pump 3 to the nozzle 9.

S7: By applying a pressure to the nozzle 9 from the pump 3 the liquid is sprayed out from the nozzle 9 from the bottom (8) of the tank into the sedimented media.

S9: When the sedimented media close to the bottom 8 of the tank has been sufficiently re-suspended the impeller 7 is started. The impeller 7 is driven until a homogenous mixture of the media slurry is achieved.

S11: When the media slurry is sufficiently mixed it is transferred to the column. If the method according to the invention should be applied for the invert transferring of media slurry, i.e. from column to storage container the same steps S1-S11 are followed with the only change that the storage container replaces the column and the column replaces the storage container.

The above embodiments are to be understood as illustrative examples of the invention. Further embodiments of the invention are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:

1. A method for suspending separation media slurry in a tank, before transferring the separation media slurry to a column or a container, comprising the steps of:

pumping liquid from an uppermost liquid phase being formed in the tank when the media slurry is sedimenting, said liquid possibly containing a small amount of media but is hereafter being called liquid;

transferring said liquid to a nozzle (9) protruding into said tank from the bottom (8) of the tank;

applying a pressure to said nozzle (9) such that said liquid is sprayed out from the nozzle (9) into the sedimented media in the tank and thereby the sedimented media starts to re-suspend;

starting an impeller (7) provided in the tank in order to stir said media slurry that already has started to re-suspend.

2. The method of claim 1, further comprising adjusting the height of an open end (6) of an adjustable pipe (5) provided inside the tank, the height being adjusted to the liquid phase of the media slurry having started to sediment, said adjustable pipe (5) being connected to said nozzle (9) through a pump (3).

3. A tank adapted to be used for suspending separation media slurry before transferring the separation media slurry to a column or a container, said tank comprising:

an impeller (7) adapted to rotate in order to mix the media slurry, a nozzle (9) provided protruding into the tank from the bottom (8) of the tank, and an adjustable pipe (5) having an open end (6) positioned in the tank, said open end being possible to adjust in position, said nozzle (9) and said adjustable pipe (5) being adapted to be connected to a pump (3) which is adapted to pump liquid from the adjustable pipe (5) when said open end (6) of the adjustable pipe (5) has been positioned in an uppermost liquid phase provided in the tank when the media slurry has started to sediment and pump said liquid, possibly containing a small amount of media but hereafter being called liquid, through said nozzle (9) back into the tank from the bottom (8) of the tank in order to start to re-suspend media that has sedimented in the tank.

4. The tank of claim 3, wherein said impeller (7) is adapted to start after the sedimented media has started to re-suspend by the introducing of the liquid from the nozzle.

5. The tank of claim 3, wherein the impeller (7) is provided close to the bottom (8) of the tank.

6. The tank of claim 3, wherein the impeller (7) is designed as a coil in the height direction of the tank.

7. A tank system comprising the tank of claim 3 and a pump (3) connected to the adjustable pipe (5) and to the nozzle (9).

* * * * *